United States Patent [19]

Quadri

[11] Patent Number: 5,049,154
[45] Date of Patent: Sep. 17, 1991

[54] ADJUSTABLE INTRA-LUMINAL VALVULOTOME

[75] Inventor: Arshad Quadri, Pittsfield, Mass.

[73] Assignee: Berkshire Research & Development, Inc., Pittsfield, Mass.

[21] Appl. No.: 390,410

[22] Filed: Aug. 7, 1989

[51] Int. Cl.$^5$ .............................................. A61B 17/32
[52] U.S. Cl. ..................................... 606/159; 606/171
[58] Field of Search ............... 606/159, 160, 170, 171; 128/751, 752

[56] References Cited

U.S. PATENT DOCUMENTS

| | | | |
|---|---|---|---|
| 518,600 | 4/1894 | Hallman | 606/170 |
| 2,655,154 | 10/1953 | Richter | 606/159 |
| 3,404,677 | 10/1968 | Springer | 128/751 |
| 4,200,111 | 4/1980 | Harris | 128/751 |
| 4,655,217 | 4/1987 | Reed | 606/159 |
| 4,768,508 | 9/1988 | Chin et al. | 606/159 |

FOREIGN PATENT DOCUMENTS 1266446 4/1968 Fed. Rep. of Germany .

Primary Examiner—Michael H. Thaler
Attorney, Agent, or Firm—Mason, Fenwick & Lawrence

[57] ABSTRACT

An adjustable intraluminal valvulotome including a hollow tubular member in which is slidably disposed a control wire. First and second spring wire elements respectively interconnect first and second cutting blades having first and second perpendicular cutting edges to one end of the control wire. There is a handle member proximate the other end of the control wire for controlling longitudinal movement of the control wire in and out of the tubular member. The handle member enables the first and second cutting blades to move from a first extended cutting position to a second retracted position. A receptacle at the distal end of the tubular member restrains the cutting blades in a fully retracted non-cutting position and prevents their engagement with the vein or valves. A method of using a valvulotome to rupture and render inoperative the valves is also disclosed.

7 Claims, 2 Drawing Sheets

ADJUSTABLE INTRA-LUMINAL VALVULOTOME

FIELD OF INVENTION

This invention relates to an intra-luminal valvulotome for vascular surgery and more particularly, to such a valvulotome whose blades can be remotely retracted, extended, and adjusted and to a method of using such a valvulotome.

BACKGROUND OF INVENTION

Many individuals, particularly the elderly, suffer from deposits which clog their arteries, more commonly referred to as atherosclerosis. Quite frequently, these deposits block or restrict the flow of blood in the arteries of the lower extremeties, which limits the flow of blood to the patient's leg and foot. Lack of blood flow and oxygen to the leg and foot may be debilitating or life-threatening to the individual, and corrective measures must be taken.

Although some individuals may be treated with medication, in most cases surgery is required. Some arterial deposits may be removed or the arteries dialated with various surgical techniques, but these procedures do not work for every patient for very long. The condition may recur, requiring further action.

One procedure which has proven effective in combating atherosclerosis is to bypass the blocked artery with another blood carrying conduit. Experimentation has lead many surgeons to use synthetic type materials for replacement arteries. Such materials include an artificial tube made from Dacron or plastic. Although temporarily suitable, these artificial conduits have a tendency to become clogged once again, and therefore their use has been restricted especially in distal bypasses.

The preferred material for an arterial bypass is one of the individual's own veins. More particularly, when the femoral artery in the leg becomes blocked, it is desirable to use the greater long saphenous vein to bypass the blocked artery.

There are two ways in which a surgeon may use the individual's own vein. The vein may be harvested from the patient's leg, removed from the patient's body, and turned end for end before resetting the vein back into the body to be used to bypass the blocked artery. Turning the vein end for end ensures that the valves are oriented in the proper direction to allow the flow of blood from the heart to the leg and foot. Although this procedure is commonly used, it interfers with the integrity of the vein and long segments of small diameter veins may become blocked in the short or long term.

A second and preferred procedure is an in-situ saphenous vein bypass. During this procedure, the vein is left in place in the patient's leg, while portions of the vein are connected to the femoral artery in such a manner as to bypass the blocked portion of the artery. If the procedure were to stop here, however, the valves in the vein would prevent the flow of blood down to the leg. Therefore, an instrument called a valvulotome has been developed which is inserted into the vein to lyse or rupture and render incompetent the valves in the bypass vein.

There are two or three valvulotome instruments available today. Each is quite similar in that it includes a small cutting blade mounted on a thin stainless steel wire. To use the instrument, the surgeon makes an incision and inserts the blade into the patient's vein. The instrument is advanced into the vein past the valve which is the farthest from the incision. When the blade of the valvulotome has been pushed past the farthest valve, the surgeon then begins pulling back on the wire forcing the blade to engage with the valve cusps thereby perforating the valve and rendering it *inoperative*.

The blades currently in use are of several shapes. One shape is a "J" or "hook-shaped" blade which has a cutting edge on the inside of the curved portion of the hook. Another popular shape is an inverted "U" or "mushroom-shaped" blade. Other shapes are also available but all are restricted in that they have only one cutting edge. Several serious complications have arisen however with the use of these types of blades. Most problematic has been that although the blade is designed to engage with and perforate the valve cusps, it also frequently engages with and perforates the walls of the vein as the blade is pulled back through the vein. Since the vein has a tremendous number of branches, there is also the danger that the blade may snag and engage with the opening leading to these branches, and lyse this junction. When this occurs, remedial surgery must be performed to correct the inadvertent and unwanted rupture.

A further problem arises in that the existing blades do not always satisfactorily lyse the valves to allow for a sufficient amount of blood to the leg and foot. Valve cusps are "cup" shaped and are hingeably attached to the vein's inner wall. When the cusps close, they contact one another and the backward flow of blood pushes these cusps securely against one another, preventing any further backward flow. Since current valvulotome blades have only one cutting edge, the value cusps may not be sufficiently disabled, or only one cusp may be disabled at one time in the case of the "J" blade.

An additional problem with the current blade designs is that the blade is of one size while the vein itself is tapered having a larger diameter near the groin area and becomes narrower near the ankle. This causes further complications in trying to perforate valve cusps without causing trauma to the inner wall of the vein. In addition, since the blade is not retractable, it cannot be pulled back once inserted into the vein without engaging with the valves or other portions of the vein.

SUMMARY OF INVENTION

It is therefore an object of this invention to provide an improved valvulotome in which the blade may be extended for cutting and retracted to a shielded position.

It is a further object of this invention to provide such a valvulotome in which extension and retraction of the blade may be controlled from a remote location outside of the body.

It is a still further object of this invention to provide such a valvulotome which minimizes trauma to the inner wall of a vein.

It is a still further object of this invention to provide such a valvulotome having more than one blade, each blade having multiple cutting edges perpendicular to each other to ensure complete perforation of the valve cusps.

It is a further object of this invention to provide such a valvulotome in which the distance between the blades may be remotely adjusted to conform to the size of the vein.

It is a still further object of this invention to provide such a valvulotome which may be retrieved once inside the vein without causing any damage to the valves.

It is a further object of this invention to provide such a valvulotome which is inexpensive to manufacture and is disposable.

It is a still further object of this invention to provide such a valvulotome which has an end member capable of shielding the cutting edge of the blades allowing the instrument to be manipulated in the vein without trauma to the vein wall or vein branches.

It is a still further object of this invention to provide such a valvulotome which has an end member capable of shielding the cutting edge of the blades allowing the instrument to be manipulated in the vein without entering the vein branches.

This invention results from the realization that a truly novel and effective valvulotome may be achieved by using a plurality of cutting blades with at least two transverse cutting edges whose separation may be varied remotely and which may be retracted into a shielded non-cutting position or extended into a cutting position, all remotely.

This invention features an adjustable intraluminal valvulotome including a hollow tubular member in which is slidably disposed a wire member. There are means for interconnecting first and second cutting blades to one end of said wire member. There are means proximate the other end of the wire member for controlling longitudinal movement of the wire member in and out of the tubular member. The means for controlling longitudinal movement of the wire member enables the first and second blades to move between a first extended cutting position and a second retracted position. Shielding means restrain the first and second cutting blades in the fully retracted non-cutting position.

In a preferred embodiment, each of the first and second cutting blades includes first and second cutting edges which are transverse to each other. The means for interconnecting the first and second cutting blades to the wire member includes first and second wire elements each element having a first end attached to said first and second cutting blades respectively, and means for joining the second end of the first and second wire elements to the wire member. Means for joining the first and second wire elements to the wire member may include a welded joint. In addition, the wire elements may be comprised of generally flat spring wire.

The valvulotome may further include means for generally indicating the distance of projection of said first and second cutting blades from the end of said tubular member. Also included may be means indicating the interblade spacing between the first and second cutting blades when in the extended position. The means for shielding may also include receptacle means for enclosing at least a portion of the first and second cutting blades.

This invention also features a method of using a valvulotome to rupture and render inoperative valves located in a vein including making an incision in a vein whose valve is to be rendered inoperative and introducing into the vein an intraluminal valvulotome having a plurality of cutting blades. The method also includes advancing the cutting blades into the vein until the cutting blades are adjacent but not beyond the valve which is to be rendered inoperative. The method further includes extending the cutting blades into a cutting position beyond the valve, and at least partially retracting the cutting blades causing the blades to engage with the valve and thereby rupture and render inoperative the valve cusps. The cutting blades are then fully retracted into a shielded non-cutting position. If additional valves are to be rendered inoperative, the valvulotome is re-positioned within the vein until the cutting blades are adjacent but not beyond a subsequent valve that is to be rendered inoperative. The steps of extending the cutting blades, engaging the blades with the valve to rupture and render inoperative the valve, and fully retracting the cutting blades to a shielded non-cutting position are repeated as required, until all the valves in the vein that are desired to be rendered inoperative have been ruptured.

The method may further include inserting into the vein an angioscope and observing when the cutting blades have been extended past the valve to be rendered inoperative. In addition, the method may further include observing the ruptured valve with the angioscope to ensure that the valve has been rendered inoperative.

DISCLOSURE OF PREFERRED EMBODIMENT

Other objects, features and advantages will occur to those skilled in the art from the following description of a preferred embodiment and the accompanying drawings, in which.

An adjustable intraluminal valvulotome according to this invention, may be accomplished by providing a hollow tubular member in which is slidably disposed a wire member. Such a wire containing hollow tubular member may be fashioned from a standard endoscopic instrument utilized for performing biopsies. An example of such an instrument is available from American Edwards and is designated as having an outside diameter of 4 F. The instruments vary in length from 80 to 100 cm. Proximate one end of the wire, is a handle of plastic or other suitable material which facilitates sliding the wire through the tube. The wire member near the plastic handle may include graduation marks to generally indicate the longitudinal distance the wire is extended outwardly from the end of the tubular member, as well as the inter-blade spacing between the two cutting blades. Typically, the blades may be extended from two to three centimeters in distance outward from the end of the tubular member, at which point the interblade spacing may be as wide as approximately 2 mm to 5 mm.

Each cutting blade is mounted on a flat spring-loaded wire element. The spring action of the wire serves to increase the interblade or radial spacing as the blades are extended longitudinally outward from the tubular member. Each wire element is joined at a common point to the wire member by means such as soldering or welding.

As the blades are retracted, a small-diameter hole or aperture in the end of the tubular member through which the wire elements pass, causes the blades to pull in closely together. As the user begins retracting the blades, the blades engage with and cut the valve cusps to render inoperative a valve within a vein. After the valve cusps have been ruptured, the blades are in a partially retracted intermediate position. The blades may be further, fully retracted into a shielded, non-cutting position. The blades may rest against a bullet or nozzle shaped end member which serves to shield the cutting edges of the blades from contact with any external surface. In a preferred embodiment, the end of the tubular member may include a receptacle which serves to surround and contain at least a portion of the two cutting blades to shield them from contact with the vein.

Each cutting blade may be made of stainless steel and electronically welded to its associated flat spring wire. The blades are approximately 3 to 4 mm in length, 2 mm in width, and 1 mm in thickness. The flat spring wire should be of appropriate size for individual attachment to the blades at one end, and attachment together to the wire member at the other end. Any edge or corner of the cutting blades which is not to be used for cutting is rounded or polished to avoid damaging the inner wall of the vein.

Figure 1:
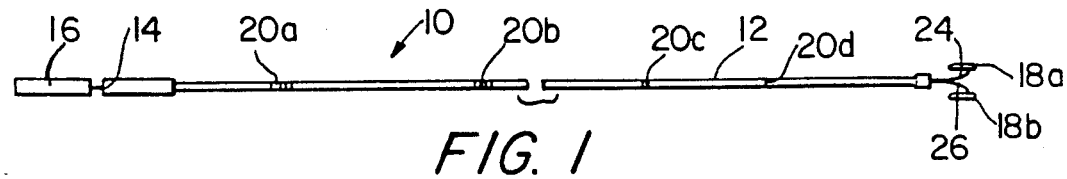
FIG. 1 is a schematic representation of the adjustable intraluminal valvulotome according to this invention.

The adjustable intraluminal valvulotome 10, FIG. 1 includes hollow tubular member 12 through which is slidably mounted wire member 14. Attached to one end of wire 14 is handle 16 while cutting blades 18a and 18b are mounted to the other end of the wire member. Hollow tubular member 12 includes markings 20a–20d which serve to indicate how far into the vein the valvulotome has been advanced.

Figure 2:
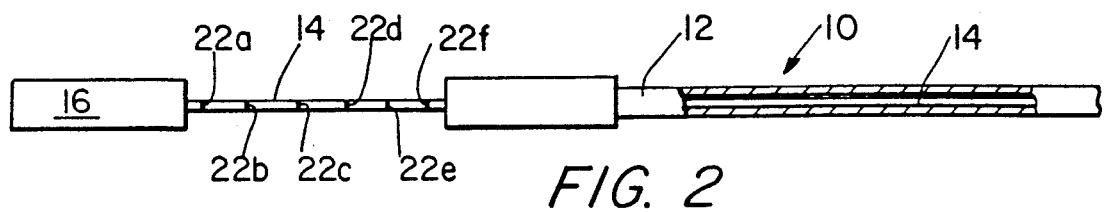
FIG. 2 is a detailed schematic view of the means for controlling the movement of the control wire and cutting blades through the hollow tubular member of the valvulotome and further showing graduation marks for gauging the extended position of the cutting blades.

Wire member 14, FIG. 2, also includes graduation markings 22a–22f which serve as a guide to indicate the interblade spacing between the two cutting blades.

Figure 3:
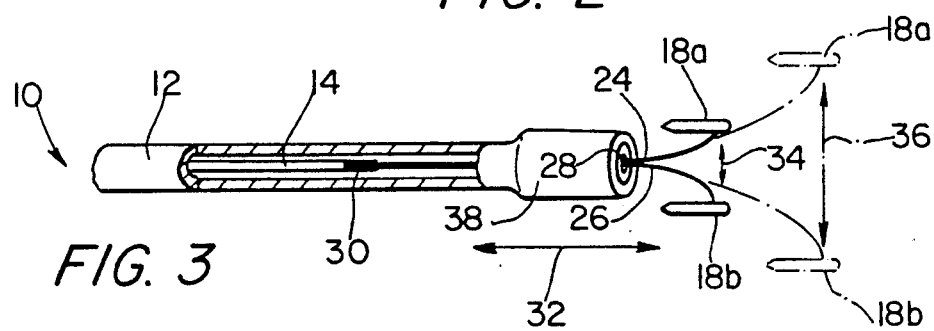
FIG. 3 is a more detailed view of the end member of the valvulotome according to this invention showing two cutting blades in the partially extended position.

Cutting blades 18a and 18b, FIG. 3, are mounted to spring wire elements 24 and 26, respectively. Wire elements 24 and 26 pass through narrow aperture 28, which serves to restrain cutting blades 18a, 18b and hold them in the non-cutting position when fully retracted. Wire elements 24 and 26 are attached to wire member 14 at joint 30. Wire element 14 is slidably movable in hollow member 12 in the direction of arrow 32. Slidably moving wire member 14 causes cutting blades 18a and 18b to extend from the intermediate position shown by interblade spacing arrow 34 outwardly to a fully extended position indicated by the dashed lines, achieving the interblade spacing indicated by dashed arrow 36.

Figure 4:
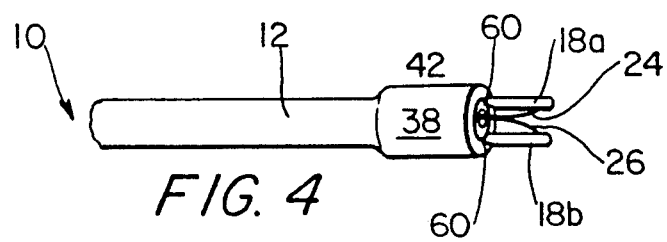
FIG. 4 is a more detailed schematic representation of an end member of the valvulotome showing the blades in the retracted position.

Hollow tubular member 12, FIG. 4, may include end member 38 having receptacle 40 which serves to shield cutting blades 18a and 18b when in the fully retracted position. Receptacle 40 may include hollowed out cavity 42 in which rests first cutting edges 44 and 46 of blades 18a and 18b respectively. Second cutting edges 48 and 50 of the blades are shielded by virtue of the fact that they are back to back facing one another and cannot come in contact with the vein or other object.

Figure 5:
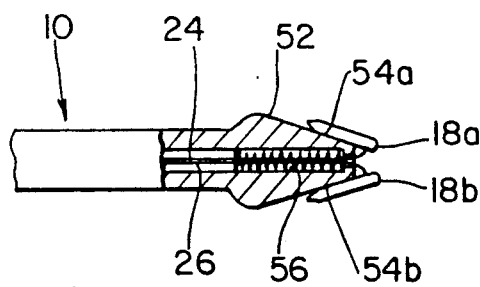
FIG. 5 is an alternative embodiment of the receptacle end of the valvulotome of this invention with the blade in the retracted position and the cutting edges secured against the receptacle.

Alternatively, end member 52, FIG. 5, may be in the form of a bullet or other tapered shape which allows cutting blades 18a and 18b to rest against side wall areas 54a and 54b of end member 52 in the tapered area which is substantially smaller than the maximum diameter of end member 52 and on its trailing end, for shielding the cutting blades in the fully retracted position. Additionally, narrow aperture 28a may be formed by coiled spring 51. Wire elements 24a and 26a pass through the center of the spring. As the blades are extended, wire elements 24a and 26a push against and expand the portion of the spring forming aperture 28a. As the blades are retracted, the spring forces aperture 28a to narrow thus keeping the cutting blades tightly against end member 52.

Figure 6:
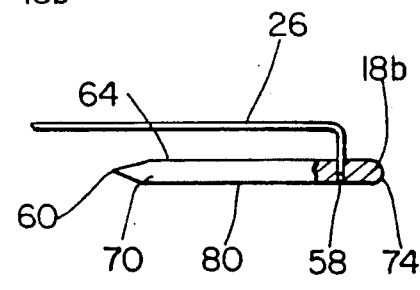
FIG. 6 is an axonometric side view of a cutting blade of the valvulotome according to this invention.
Figure 7:
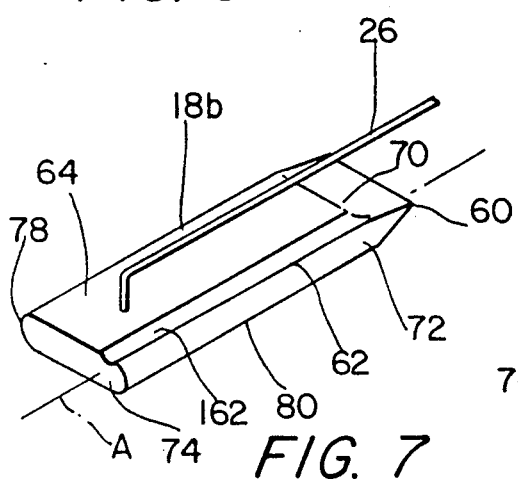
FIG. 7 is a schematic representation of a cutting blade for a valvulotome according to this invention showing a base cutting edge and a vertical cutting edge formed by grinding a channel in the blade.
Figure 8:
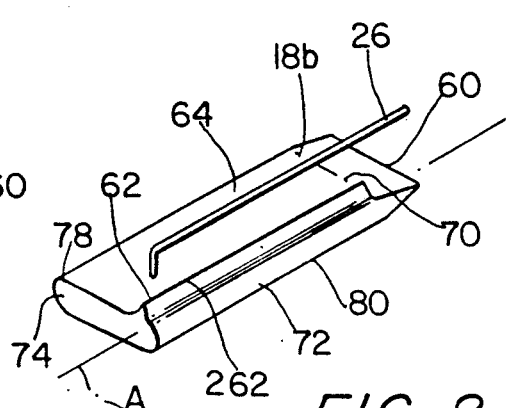
FIG. 8 is an alternative embodiment of the cutting blade for a valvulotome according to this invention showing a vertical cutting edge formed by a protrusion on a planar surface of the blade.

Cutting blade 18c, FIG. 6, is shown attached to flat spring wire element 56. Spring wire element 56 may be inserted through hole 58 in blade 18c and welded into position. Blade 18c, FIG. 7, includes first cutting edge 60 along the base of the blade, as well as second cutting edge 62 transverse to cutting edge 60 and generally parallel to longitudinal axis 63 of cutting blade 18c. Cutting edge 62 may be fashioned by grinding depression 64 on blade 18c or alternatively, may be fashioned by providing a raised cutting edge 66, FIG. 8, also aligned with longitudinal axis 63a of cutting blade 18c. All remaining edges such as 68a and 68b of cutting blade 18c are well-rounded to avoid sharp edges which might damage the inner wall of a vein.

Figure 9:
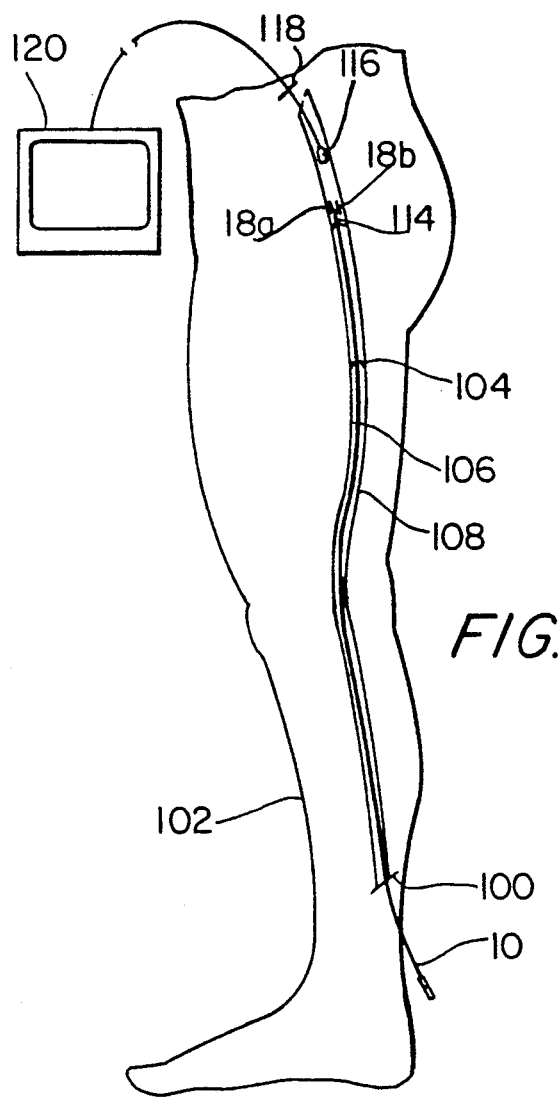
FIG. 9 is a schematic representation of a leg with a blocked femoral artery which has been bypassed with a vein in which has been inserted a valvulotome and angioscope.

The method of using the intraluminal valvulotome according to this invention includes making incision 100, FIG. 9, in leg 102 proximate vein 104 that has been used to bypass blockage 106 in artery 108. The adjustable intraluminal valvulotome 110 is inserted through the incision and advanced into vein 104 to a distance that places end member 38 adjacent to but not beyond valve 114 which is to be rendered inoperative. If a number of valves are to be ruptured, the valvulotome 110 may be inserted up to the farthest valve and then the valves may be ruptured in sequence starting with the farthest valve first and ending with the valve nearest the incision. Angioscope 116 may be inserted through incision 118 and may be used to monitor the position of cutting blades 18a, 18b on monitor 120.

Figure 10:
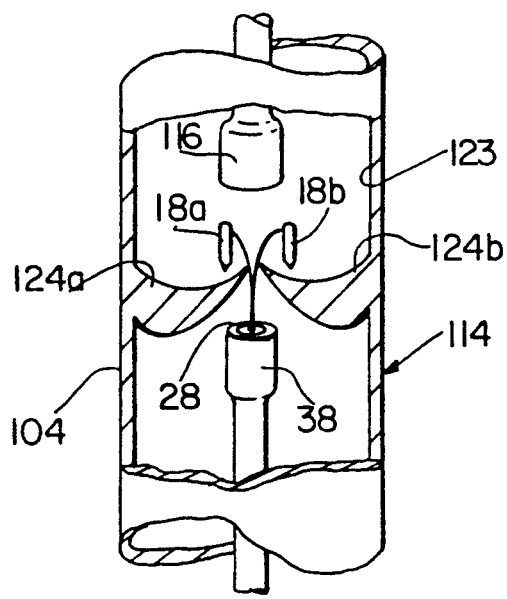
FIG. 10 is a lateral cross sectional view of a vein with venous valve in which has been inserted the valvulotome according to this invention along with an angioscope.
Figure 11:
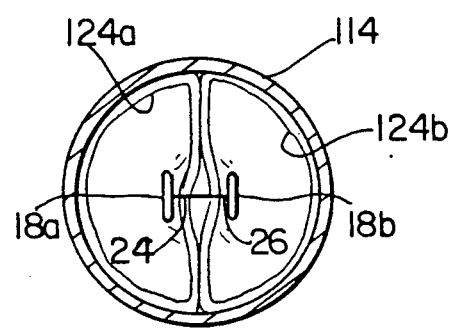
FIG. 11 is a cross sectional view of the vein and venous valve of FIG. 10 showing the engagement of the blade cutting edges with the valve cusps.
Figure 12:
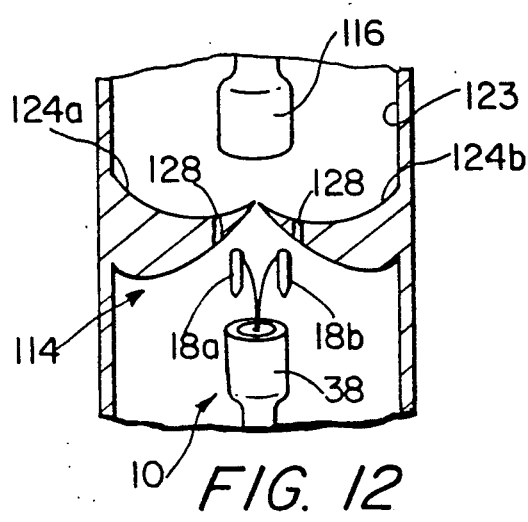
FIG. 12 is a cross sectional view of the vein and venous valve of FIG. 10, showing retraction of the cutting blades after engaging with and rupturing the valve cusps.
Figure 13:
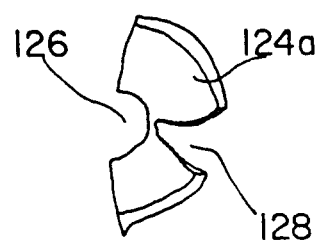
FIG. 13 is a detailed view of a single ruptured valve cusp.

Once valvulotome end member 38, FIG. 10, has been advanced proximate valve cusps 124a, 124b of valve 114, cutting blades 18a and 18b are extended longitudinally and radially outward beyond valve cusps 124a, 124b until interblade spacing shown by arrow 121 is sufficient to engage with the valve cusps 124a, 124b, but not too wide so as to damage inner wall 123. Angioscope 116 may be used to monitor the positioning and extension of the blades, FIG. 11. Cutting blades 112a, 112b are then retracted, FIG. 12, causing the blades to engage with and cut valve cusps 124a, 124b along lines 126, 128, FIG. 13, rupturing the valve cusps and rendering valve 114 inoperative. Cutting blades 18a, 18b may then be fully retracted into a completely shielded position. Valvulatome end member 38 may then be repositioned proximate the next valve to be rendered inoperative. The surgeon repeats the steps of extending the cutting blades beyond the valve cusps and retracting the blades, causing them to engage with, cut and rupture the subsequent valve cusps. This procedure is repeated for each of the valves that are to be rendered inoperative. As an aid to the surgeon, angioscope 116 may be utilized to ensure that all the valves have been properly ruptured. Most importantly, if the surgery needs to be aborted, the valvulotome with cutting blades 18a, 18b, in their fully retracted and shielded position, may be withdrawn from the vein without any damage to the valve cusps or the inner walls of the vein.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An adjustable intraluminal valvulotome comprising:
    a hollow tubular member having a distal end and a proximal end;
    first and second opposed cutting blades movable between an extended position and a retracted position with respect to said distal end of said tubular member and between an open position in which said cutting blades are spaced apart from each other and a closed position in which said cutting blades are drawn close to each other, said cutting blades being in said closed position when in said retracted position and in said open position when in said extended position, each of said cutting blades having an inner surface, an outer surface, a forward blunt edge in the direction of extension, a rearward cutting edge in the direction of retraction, and a pair of opposed side edges, one of said side edges being a blunt edge and the other of said side edges being a cutting edge, said inner surfaces of said cutting blades substantially facing each other in all said positions;
    control means slidably disposed within said hollow tubular member for moving said first and second cutting blades between said extended and retracted positions and a plurality of partially-extended positions intermediate said extended and retracted positions;
    spacing means for moving said first and second cutting blades laterally apart from each other from said closed position to said open position as said control means moves said cutting blades from said retracted position to said extended position and for drawing said first and second cutting blades back towards each other from said open position to said closed position as said control means moves said cutting blades from said extended position to said retracted position; and
    shielding means for shielding at least said rearward cutting edges of said first and second cutting blades in said retracted and closed positions.

2. The valvulotome of claim 1, wherein said side cutting edges extend inwardly from said inner surfaces of said cutting blades, whereby said side cutting edges are shielded from contact with any surrounding tissue when said cutting blades are in said closed position.

3. The valvulotome of claim 1, wherein said spacing means comprises biasing means for biasing said first and second cutting blades laterally apart from each other.

4. The valvulotome of claim 3, wherein said biasing means comprises first and second spring wire element slidably disposed within said hollow tubular member, each of said first and second spring wire elements having proximal and distal ends, said distal ends of said first and second spring wire elements being attached to said first and second cutting blades, respectively.

5. The valvulotome of claim 4, wherein said biasing means further comprises a coiled spring axially disposed in said hollow tubular member, said first and second spring wire elements being slidably disposed within said coiled spring.

6. The valvulotome of claim 4, wherein said control means comprises a single wire element connected to said proximal ends of said first and second wire elements.

7. The valvulotome of claim 1, wherein said shielding means comprises receptacle means formed at said distal end of said tubular member for enclosing at least a portion of said first and second cutting blades.

* * * * *